United States Patent [19]

Tomantschger et al.

[11] Patent Number: 5,302,274

[45] Date of Patent: Apr. 12, 1994

[54] ELECTROCHEMICAL GAS SENSOR CELLS USING THREE DIMENSIONAL SENSING ELECTRODES

[75] Inventors: Klaus Tomantschger, Mississauga, Canada; Allan A. Janis, Snyder, N.Y.; Norman L. Weinberg, East Amherst, N.Y.; Joseph M. Rait, Buffalo, N.Y.

[73] Assignee: Minitech Co., Buffalo, N.Y.

[21] Appl. No.: 915,263

[22] Filed: Jul. 20, 1992

Related U.S. Application Data

[63] Continuation-in-part of Ser. No. 513,441, Apr. 16, 1990, Pat. No. 5,173,166.

[51] Int. Cl.$^5$ .......................................... G01N 27/416
[52] U.S. Cl. ............................. 204/412; 204/415; 204/425; 204/426; 204/427; 204/431; 204/432
[58] Field of Search .............. 204/431, 432, 412, 424, 204/425, 426, 427

[56] References Cited

U.S. PATENT DOCUMENTS

| | | | |
|---|---|---|---|
| 4,025,412 | 5/1977 | LaConti | 204/424 |
| 4,227,984 | 10/1980 | Dempsey et al. | 204/408 |
| 4,394,239 | 7/1983 | Kitzelmann et al. | 204/414 |
| 4,522,690 | 6/1985 | Vankatasetty | 204/153.19 |
| 4,543,273 | 9/1985 | Handa et al. | 427/126.3 |
| 4,718,991 | 1/1988 | Yamazoe et al. | 204/153.1 |
| 4,876,115 | 10/1989 | Raistrick | 427/115 |

OTHER PUBLICATIONS

Hackh's Chemical Dictionary, Fourth Edition, McGraw-Hill Book Company, New York, 1969, p. 622.

Ebonex Electrodes for Electrometallury, Product Description, 4 pages; Ebonix Technologies, Inc.

*Primary Examiner*—T. Tung
*Assistant Examiner*—William T. Leader
*Attorney, Agent, or Firm*—Donald E. Hewson

[57] ABSTRACT

An electrochemical gas sensor cell is provided, the use of which permits quantitative measurement of volatile gas contaminants in an atmosphere being monitored. The cell comprises at least a first sensor electrode and a second counter electrode, on either side of an ion conductive electrolyte which may be immobilized in a matrix. The electrolyte may also be a solid electrolyte or a polymer electrolyte. The sensing electrode has a high surface area catalyst dispersed on a porous substrate, and is mounted in such a manner as to be exposed to the atmosphere which is to be sensed for gaseous contaminants, with the counter electrode being isolated from any exposure to that atmosphere. Generally, the electrodes are mounted in electrically conductive frames, sandwiching a third non-conductive frame member in which the ion conductive electrolyte is substantially located. The conductive frames may comprise electronically conductive materials such as conductive polymers, ceramics, nitrides, oxides and graphites. In an alternative embodiment, a further reference electrode may be mounted so as to be exposed to the electrolyte. The porous electrode may comprise a porous substrate or a base layer, a catalytically active metal, alloy, or metal oxide (usually a noble metal) dispersed in a high surface area form, carbon, and a polymeric hydrophobic binder.

29 Claims, 4 Drawing Sheets

ELECTROCHEMICAL GAS SENSOR CELLS USING THREE DIMENSIONAL SENSING ELECTRODES

CROSS REFERENCE

This application is a Continuation-In-Part of application Ser. No. 07/513,441 filed Apr. 16, 1990, now U.S. Pat. No. 5,173,166.

FIELD OF THE INVENTION

This invention relates to electrochemical gas sensor cells. In particular, the invention relates to gas sensor cells which, by the choice of catalyst and electrolyte, may be used in circumstances to sense the presence of a gas contaminant in an atmosphere. The electrochemical gas sensor cell has a specific electrical characteristic developed between a sensor electrode and a counter electrode or a reference electrode, which characteristic will be indicative of the amount of the gas contaminant that is present. The present invention also teaches porous electrodes whose use in the gas sensor cells makes them particularly effective.

BACKGROUND OF THE INVENTION

In human inhabited environments, and in environments where other dangers such as explosion, fire or toxicity may occur, there is very often a requirement to test for gas contaminants which may create a health or safety hazard. In particular, there is an increasing demand for devices to monitor a specific-atmosphere—generally an enclosed volume—for toxic or flammable gases. Also, particularly where the atmosphere being monitored is inhabited by humans, there is a specific requirement for sensors having a rapid and reliable response to such contaminating gases as carbon monoxide, oxides of nitrogen, sulfur dioxide, hydrogen sulphide, carbon dioxide, hydrogen, phosphine, arsine, methanol, volatile hydrocarbons, and so on. Any such gas requires a specific sensor cell design, and in any given installation there may be several sensor cells of the present invention installed; each installed sensor cell having electrolytes and catalysts chosen for each of the sensor cells to be reactive to the presence of specific contaminating gases being tested for.

In some circumstances, the enclosed volume being monitored may be monitored only for one or two specific contaminating gases, which gases are the only likely gas contaminants to occur in such atmosphere being monitored. An example may be storage rooms where hazardous chemicals may be kept, or production facilities where hazardous materials are being released or are being used in the manufacture of other materials. In that case, the possible gas contaminants are known and specific cell systems may be designed accordingly.

To satisfy the requirement to be able to monitor for the presence of gas contaminants, it is not only necessary that sensor cells be provided that are capable of being economically produced and therefore readily purchased, it is also necessary that such sensor cells shall have a reasonably long active lifetime when installed in place. Moreover, particularly where it is necessary to monitor for toxic or flammable gases where there may be humans in the environment being monitored, or where there is a specific hazard, such sensors cells may be capable of detecting the presence of low concentrations of contaminant gases being tested for, so as to provide sufficient warning before the concentration of contaminant gas reaches dangerous levels.

The present invention provides gas sensor cells that have a catalytically active sensor electrode which is exposed to the atmosphere being monitored; where the sensor electrode is separated from a counter electrode which may also function as a reference electrode, or a counter electrode and a reference electrode, by a suitable ion conductive electrolyte. The nature of the electrolyte, and the manner in which it is retained in position, is discussed hereafter. It is important, however, that the sensor electrode must be sufficiently sensitive to low concentrations of gas contaminants in the atmosphere being tested, and examples of such electrodes are discussed hereafter.

The present invention provides a structure for the electrochemical gas sensor cells which is essentially of a sandwich-type construction, where the outer frame members secure the electrodes in place, and sandwich a third frame member between them in which all or at least a portion of the electrolyte is located. In the usual embodiments, the outer frame members are electrically conductive, so as to exhibit specific conductivity characteristics; and also so as to provide means for connecting external electrical measuring means (or, in yet another alternative embodiment, an external power source) directly to the sensor cell frame members. Moreover, the outer frame members of the electrochemical sensor cell of the present invention provide means for sealing the structure together, and thereby sealing means for the electrolyte chamber, as discussed hereafter. The third, intermediate, frame member is not electrically conductive, and it may be significantly thinner than the outer frame members.

Among the gases that may be tested for are gases and volatile substances as diverse as carbon monoxide, carbon dioxide, oxides of nitrogen, oxides of sulfur, hydrides of nitrogen such as ammonia and hydrazine, hydrides of phosphorus, sulfur, arsenic or boron, mercaptans, aldehydes, hydrogen, unsaturated and saturated hydrocarbon vapours, halocarbons and alcohols such as methanol. Indeed, in general a specific cell system can be devised using suitable catalysts and electrolytes to test for any toxic, combustible or flammable gas, or generally volatile substances which may be oxidizable. The enclosed volumes within which such gas contaminant monitoring may take place include those suggested above, and as well ordinary residential housing, parking garages of all sorts, vehicles, interiors of commercial or industrial buildings, hospitals, and mines.

Prior art devices have included various patented devices such as those described below; and in any event the prior art may generally be defined as comprising electrochemical sensors, ionization chamber sensors, photoelectric types of sensors, and metal oxide semiconductor devices. Most prior art sensors are solid stat or solid electrolyte, and may employ stabilized zirconia, yttria and tin oxides. However, any sensors that has heretofore been used for monitoring and/or controlling gas atmospheres has exhibited one or more of the following disadvantageous characteristics: (a) they most often have quite complex structures; (b) they very often must operate or can only operate at elevated temperatures (e.g. from 150° C. to 600° C.); (c) as well, or as a consequence of the above, they may require outside sources of electrical energy and/or heat to maintain their operating temperatures; (d) it follows that such devices may have long start-up or warm-up periods before reaching their operating characteristics; (e) moreover, nearly all prior art devices are costly to build and/or to operate; (f) and finally, the prior art devices are subject to deterioration over time, due to gas poisoning of their sensing systems and/or sensing elements.

Several specific prior art gas sensing elements or cells are as follows:

LaCONTI U.S. Pat. No. 4,025,412 describes a gas sensor which is capable of detecting oxidizable gases in air. The sensor cell is a laminated filter design, in which approximately ten components are used, placed on top of one another. The assembly is very expensive to produce, even in quantities, and the structure is susceptible to electrolyte leakage.

DEMPSEY et al, U.S. Pat. No. 4,227,984 provides a gas sensor having a solid polymer electrolyte, and being arranged so that a fixed potential difference between the reference and sensing electrodes is present at all times. The particular purpose of the Dempsey et al structure is to preclude the necessity for temperature compensation. DEMPSEY et al describe the use of noble metal and their alloys, or graphitic catalytic electrodes, whereby the catalyst particles are bonded to polymers such as PTFE. Thus, the electrodes comprise catalyst particles bonded to particles to a hydrophobic polymer, and as such they do not utilize a three dimensional sensing electrode active layer.

KITZELMANN et al, U.S. Pat. No. 4,394,239 teach an electrochemical sensor which is particularly adapted for detecting carbon monoxide. The electrochemical cell is enclosed in a plastic body, which serves only as a cell housing. Electrical connections are achieved by means of wires which are attached to the metal mesh embedded in the sensor and reference electrodes. Moreover, the acidic electrolyte is corrosive, thus expensive metals such as platinum have to be used as current collectors and electrical leads, resulting in increased costs. However, such metals are hydrophilic, which may result in electrolyte loss. KITZELMANN et al immobilize their electrolyte by forming a gel.

As to the KITZELMANN et al electrode, it is a sensing and counter electrode which contains platinum mesh as a current collector on the gas side. The platinum mesh contacts a carbon fleece, which has a layer of platinum black coated on it, and which contacts the immobilized electrolyte. The electrode-electrolyte-gas interface is a two dimensional zone which has an area substantially identical to the geometrical area of the electrode used. KITZELMANN et al make reference to conventional gas diffusion electrodes (col. 3, lines 1-8) which could require the sensing gas to be delivered into the sensing electrode under pressure, or which may be required to be rendered hydrophobic to avoid spilling of electrolyte.

VENKATASETTY, U.S. Pat. No. 4,522,690, in a structure intended particularly for sensing the presence of carbon monoxide, requires the use of a gelled aprotic organic non-aqueous electrolyte in which the contaminant gas to be detected is soluble together with platinum sensor and counter electrodes, and a silver reference electrode. VENKATASETTY utilizes a platinum film as the active part of the sensing electrode, and in the same manner as KITZELMANN et al, thus uses a two dimensional reaction-interface approach. Moreover, the VENKATASETTY structure is extremely expensive to produce, even in quantities.

HANDA et al, U.S. Pat. No. 4,543,273 teach a structure for sensing carbon monoxide, where a solid oxide electrolyte is used. The patent, however, relates particularly to the production of the sensing element, at very high temperatures (above 600° C.). The sensor utilizes changes of conductivity of the sensing elements in the presence of gas contaminants so as to sense their concentration.

YAMAZOE et al, U.S. Pat. No. 4,718,992, describe a proton conductor gas sensor for the detection of hydrogen or carbon dioxide. In the sensing device, a pair of electrodes that are connected by a proton conductor are short circuited to cause protons to travel through the proton conductor. The difference in activity between the electrodes, or the difference in gas permeability between the electrode and the atmosphere, is used to detect various gas contaminants. The potential difference created within the proton conductor due to the proton movement is used as sensor output which is proportional to the concentration of the gas contaminant, and is relatively insensitive to humidity changes.

Co-pending application Ser. No. 07/513,441, referred to above, describes a novel sensor cell design where the cell is encapsulated. In that cell, conductive and non-conductive plastic materials are used from the sensor cell housing the plastic sensor cell is capable of making quantitative measurement of volatile gas contaminants at ambient temperatures below 100° C.

In contradistinction to the above, the present invention provides sensitive electrochemical cells, and the electrodes for use therein, which will detect the presence of low concentrations of contaminating gases in air or other environments where they may be a possibility of dangerous or hazardous accumulations of such contaminating gases. These cells, and their electrodes, have the following advantageous characteristics: (a) the structure, and their production, are very simple; (b) they operate at various temperatures and do not require temperature control, nor do they require heaters to reach operating temperature; (c) they have a fast response time; (d) they have a high activity level, by which they may become active in the presence of very low concentrations of contaminating gas; (e) they are stable in their operation; (f) they have a long operating life; (g) and finally, they are inexpensive to produce.

The present invention provides an electrochemical gas sensor cell for quantitative measurement of gas contaminants in an atmosphere being monitored. In several of the preferred embodiments, the temperature of the gas atmosphere may be significantly higher than 100° C. In any event, the gas sensor cells can be operated at temperatures up to the latent boiling or melting temperature of any of the sensor components being used. The gas sensor cell has a first sensor electrode mounted in a first frame member, a second counter electrode mounted in a second frame member, and a third frame member which contains an electrolyte chamber, where the first and second frame members are at opposite sides, respectively, of the third frame member which substantially contains the electrolyte. The manner in which the electrolyte is retained is such as to substantially accommodate changes in temperature or humidity of the atmosphere. Each of the first, second, and third frame members are formed of materials which are inert and impervious to the electrolyte. Those materials may be plastics, such as polypropylene, polyvinylidene difluoride, or acrylonitrile butadiene styrene (ABS), any of which may be filled with metals, carbon or graphite, or combinations thereof. Other suitable materials include ceramics which can be electrically non-conductive ceramics such as boron nitride, aluminum oxide, silica, or glass; or electrically conductive ceramics such as EBONEX ™—which is essentially $Ti_xO_{2x-1}$, where $x=4$ to 10 (usually $x=4$)—or other metal oxides, carbides, or sulfides, etc., may also be used.

At least the first sensor electrode, and optionally the second counter electrode is a porous electrode, with the first sensor electrode and optionally the second counter electrode having a catalyst dispersed thereon.

The sensor electrode is mounted in the first frame member so as to be exposed to the atmosphere being monitored, and the counter electrode is mounted in the second frame member so as to be isolated from any exposure to that atmosphere. Conductor means are associated with each of the first and second electrodes, and are connected to electrical measurement means and may also be optionally connected to additional electrical devices such as control or warning devices.

Thus, when the atmosphere being monitored contains a gas contaminant for which the catalyst on at least the sensor electrode and the electrolyte have been chosen to produce a change in the electrical characteristics of the sensor electrode with respect to the counter electrode in the presence of that gas contaminant, the electrical measurement means detects the change of electrical characteristic in such circumstances, the change of electrical characteristic being indicative of the presence of the gas contaminant being tested for. In that sense, the electrical characteristic may optionally provide a display of contaminant concentration, it may trigger a warning or control device, or it may be stored in a storage or memory device for later comparison and review. What that means is that electrical characteristic may be a potential which changes between the sensor electrode and the counter electrode, or the current flowing between those electrodes may change.

In an alternative embodiment, a reference electrode is located so as to be exposed to the electrolyte, and potentiometric measurement means are provided between the sensor electrode and the reference electrode, as well as the electrical measurement means being between the sensor electrode and the counter electrode.

The electrolyte may be immobilized by being absorbed in a matrix contained within the electrolyte chamber, or it may an ionically conductive solid polymer or ceramic electrolyte, or it may be a solid electrolyte capable of ionic motion within a solid lattice. Moreover, the electrolyte chamber may be in communication with an electrolyte reservoir which is formed within the third frame member, above the electrolyte chamber. Moreover, the electrolyte chamber may also extend into the first and second frame members.

Each of the first and second frame members may be electrically conductive plastics materials, or suitable polymer composites, or electrically conductive ceramics. The plastics materials of the frame members may be such as polypropylene, polyvinylidene difluoride, or acrylonitrile butadiene styrene (ABS), any of which may be filled with metal, carbon or graphite, or combinations thereof.

Other suitable stable and impervious polymers include polyvinyl chloride or acrylonitrile butadiene; suitable electrically conductive inert filler materials include titanium oxide, tungsten carbide and the like. Other inert conducting polymers may be such as those described in the *Handbook of Conducting Plastics*, Volumes 1 & 2, Marcel Dekker, 1986.

Certain suitable materials for use in the conductive frame member may be conductive ceramics such as EBONEX, (comprising $Ti_4O_7$), other conductive titanium oxide compositions such as $Ti_5O_9$ and TiO, other inert conductive metal oxides, i.e. $Na_2WO_3$ carbides (e.g., WC, TiC, ZnC, $Cr_3C_2$, etc.), sulfides (e.g., $WS_2$, $MoS_2$, etc.) borides and graphites, carbon and graphites, etc. as well as their mixtures such as TiC+C and doped materials.

In specific embodiments of the present invention, the second counter electrode may be exposed to a contained volume of cleaned or scrubbed air or other suitable gas which is substantially free of the gaseous contaminant being tested for. Moreover, in those circumstances the counter electrode is non-polarizable under ordinary operating conditions.

In a further embodiment of the present invention, the non-conducting polymer of the third frame member may have its surface plated with a suitable inert metal film such as gold, silver, platinum, or the like.

Potentiometric electric measurement means may be provided, whereby a change in the voltage developed between the sensor electrode and the counter electrode may be detected and measured. The electrical measurement means may also be amperiometric.

The catalyst, or the specific catalyst for each of the sensor electrode and optionally the counter electrode, is dispersed on the porous electrode substrate in such a manner as to have a high surface area. The catalyst of choice may be a high surface area noble metal supported or carbon, carbides, or other conductive substrates.

Still further, the present invention provides porous electrodes which may comprise at least one porous layer containing a catalytically active metal, alloy, or metal oxide—usually comprising at least one noble metal—carbon, and a polymeric hydrophobic binder. These electrodes may then be used in gas sensors according to the present invention, together with a stabilized liquid electrolyte or other suitable electrolyte; and are such that they may operate at ambient temperatures such as room temperature without the necessity for a prolonged start-up or warm-up period.

In the case of the electrolyte being a solid polymer or an ion conductive solid state material, an appropriate amount of electrolyte may be incorporated into the electrode during the fabrication process to facilitate "wetting" of the electrocatalyst. Alternatively, the finished electrode may be impregnated by the electrolyte in its liquid form—for example, DuPont NAFION ™ dissolved in alcohol, or solid state salts in their molten form or dissolved in a suitable solvent. In any event, the objective is to create a three dimensional interface between the electrolyte, the electrocatalytically active sites, and the gas contaminant within the sensing electrode, so as to increase the sensitivity and reactivity of the sensing electrode based on the geometrical electrode surface area.

The present invention also provides methods for making the electrochemical gas sensor cell, where the assembly method may be such that the assembled frame members are exposed to heat at a temperature of less than about 400° C. for a predetermined period of time, depending on the material being used. Indeed, particularly when plastic frame members are to be used, the methods of the present invention to provide the electrochemical gas sensor cell may be carried out at the relatively low processing temperature of about 165° C., or they may carried out in an induction furnace; or when the surfaces of the frame members which face each other are coated with a titanium oxide powder, the assembly may take place using microwave technology.

Indeed, the electrochemical gas sensor cell of the present invention may be produced by injection moulding the exterior frame members around the other members of the cell which are already held in place within an injection mould.

In the case where at least one of the frame members is made entirely without the use of plastic materials—such as in the case of EBONEX conductive frame members—the sensor cell can be assembled by applying an inert adhesive such as a pressure sensitive adhesive onto the frame members to be joined. Then, the sensor cell can be assembled by merely applying slight pressure at room temperature to activate the pressure sensitive adhesive used. Of course other inert adhesives, epoxides, or hot melts can be utilized as well.

By all of the above, the present invention provides a low cost electrochemical gas sensor cell which may be arranged by the choice of suitable and specific catalysts and electrolytes to sense low concentrations of specific gases being tested for, and provide a rapid and reliable response in the presence of such gaseous or volatile contaminant.

BRIEF DESCRIPTION OF THE DRAWINGS

All of the above is described in greater detail hereafter, in association with the accompanying drawings, which are intended for purposes of illustration only and are not intended to be indicative of the scale of any specific cell according to the present invention. In the drawings.

DESCRIPTION OF THE PREFERRED EMBODIMENTS

It should be noted, first, that the present invention permits the use of porous electrodes which comprise at least one porous layer containing a finely dispersed high surface area suitable catalyst. The catalyst may be a catalytically active noble metal, such as platinum, palladium, iridium, etc.; or an alloy such as Pt/Pd, Pd/Rh, or Au/Ru; or it may be an organometallic compound containing elements such as cobalt, iron or nickel. The catalyst may be unsupported; or it may be supported on materials such as carbon or graphite, or carbides, EBONEX, or combinations thereof, all with a suitable polymeric hydrophobic binder. The electrode structure may optionally include a metallic mesh current collector.

The simplest or basic structure of an electrochemical gas sensor cell 10, according to the present invention, is as follows: a first sensor electrode 12 is mounted in a first frame member 14, a second counter electrode 16 is mounted in a second frame member 18, and a third frame member 20 has within it an electrolyte chamber 22. An ion conductive electrolyte 24 is substantially contained within the electrolyte chamber 22, which is defined at its sides by the first and second frame members 14 and 18 together with the sensor electrode 12 and the counter electrode 16.

The electrolyte 24 is retained within the third non-electrically conductive frame member 20 in such a manner as to substantially accommodate changes in temperature or humidity of the atmosphere. The electrolyte chambers may also extend partially into either or both of the frame members 14 and 18. Moreover, the electrolyte chamber 22 may be packed with a suitable matrix such as cellulose, titanate, asbestos, or DARAMIC TM, and then after the cell is assembled (such as by one of the modes of assembly discussed hereafter) a liquid electrolyte may be injected into the electrolyte chamber 22 through a passage 26, after which a plug 28 may be inserted. The electrolyte may be phosphoric acid or sulphuric acid, possibly diluted with distilled water; or it may be methanesulphonic acid, or a more neutral pH electrolyte such as aqueous phosphate or sulphate salt solutions; or combinations of all of the above. The electrolyte may be gelled by conventional gelling agents such as CMC. Alternatively the electrolyte may be a solid polymer electrolyte, for example a cationic or anionic resin polymer such as NAFION.

The electrolyte may also constitute ionically conductive solid materials such as $MAg_4I_5$ (M = Rb, K, or Pb), zirconium dioxide ($ZrO_2$), zirconium phosphate ($H_2ZrP_2O_8.H_2O$), uranyl hydrogenphosphate tetrahydrate (HUP$_2$. PO$_4$.4H$_2$O) {HUP}, antimonic acid ($Sb_2O_5.nH_2O$), $Ag_6I_4WO_4$, Na beta-alumina, Nasicon ($Na_3Zr_2Si_2PO_{12}$), lithium iodide LiI, as well as other ionically conductive ceramics. These substances can be used singly or in combination with other ionically conductive compounds, and can optionally be processed with the addition of a binder.

In each of the embodiments of FIGS. 1 to 7, the sensor electrode 12 is mounted together with the first frame member 14 in such a manner that the electrode 12 is exposed to the atmosphere. That is accommodate, for example, by a passage 30 through which the gaseous atmosphere may flow as indicated at arrow 32. The counter electrode 16, on the other hand, is mounted in the second frame member 18 in such a manner that it is isolated from any exposure to the atmosphere.

Figure 1:
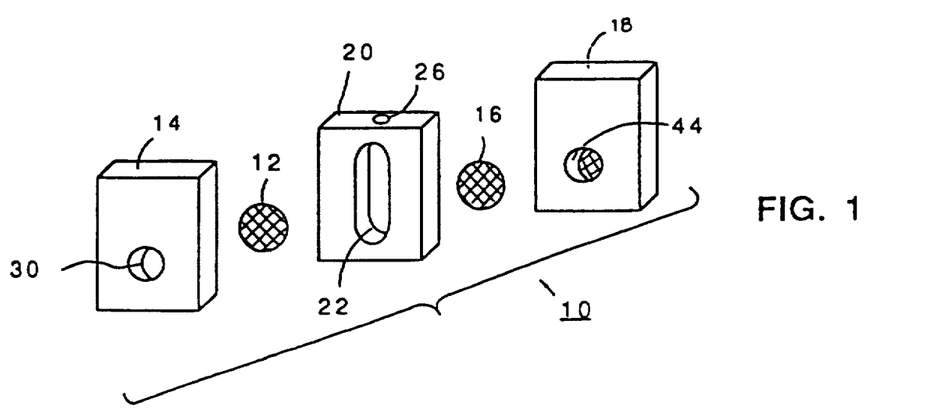
FIG. 1 is an exploded view of a typical assembly of an electrochemical sensor cell according to the present invention.
Figure 2:
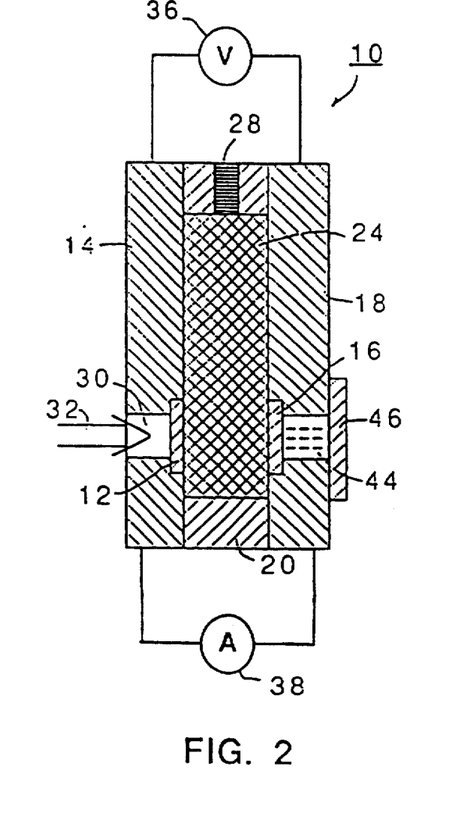
FIG. 2 is a schematic cross-section, not-to-scale, of a first embodiment of a sensor cell, showing alternative arrangements for electrical measuring means associated with the cell.
Figure 3:
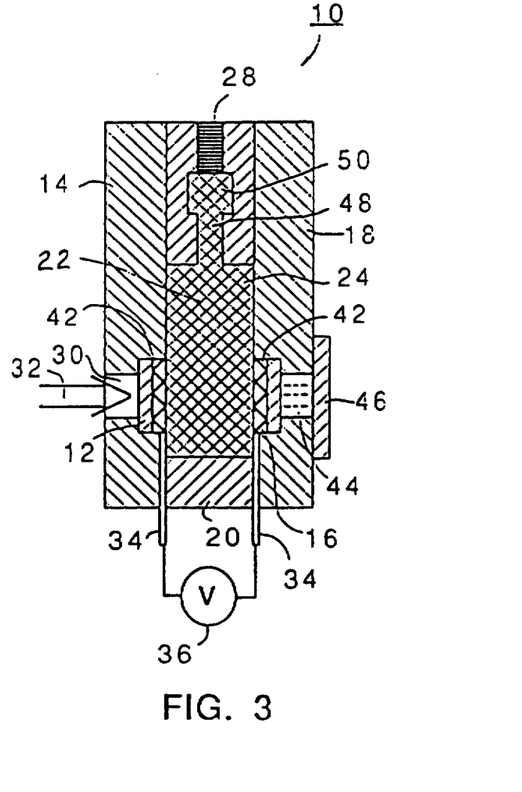
FIG. 3 to 7 show, in schematic manner, alternative assembly features of other electrochemical cell configurations in keeping with the present invention.

Clearly, in order for there to be sensing of electrical potential between the electrode 12 and 16, there must be conductive means associated with them, and there must be electrical measurement means provided. In general, the material of the first and second frame members 14 and 18 is an electrically conductive material, as discussed hereafter, so that the frame members provide the conductor means away from the electrodes 12 and 16 themselves. Alternatively, conductor means such as flat wire or metallic tape 34, as indicated in FIG. 3, may be utilized. In that case, the conductors 34 are physically and electrically connected to the electrodes 12 and 16, and in that instance the first and second frame members 14 and 18 need not necessarily be themselves made of a conductive plastics material.

The electrical measurement means between the electrodes 12 and 16 may be such as voltmeter 36; or, when the electrochemical gas sensor cell is such that it may provide a measurable current in the order of a few microamps or milliamps, for example, an ammeter 38 together may be utilized. Thus, potentiometric or galvanostatic, as well as amperiometric measuring means can be provided to sensor electrode 12 and the counter electrode 16 in the presence of a gas contaminant for which the particular cell system, including the catalyst on the electrodes 12 and 16 and the electrolyte 24, has been chosen.

In the simplest terms, in the presence of a gas contaminant as mentioned immediately above, there will be a change in the electric potential of the sensor electrode 12 with respect to the counter electrode 16, and it is that change and the detection and measurement thereof which are indicative of the presence of the gas contaminant.

The material of the first and second frame members 20 may be an inert polymer typically comprising polypropylene, polyvinylidene difluoride, or acrylonitrile butadiene styrene (ABS), filled with metal, carbon or graphite, or combinations thereof. Of course, the material of the first and second frame members may also be any of those discussed previously, including polyvinyl chloride or acrylonitrile butadiene styrene; and other suitable electrically conductive filler materials include titanium oxide (EBONEX ceramic), and tungsten carbide.

Still other conductive materials may, as noted above, be conductive ceramics or other inert conductive metal oxides. Indeed, even poorly electrically conductive materials may be used.

Typically, the inert electrically conductive materials used may have a specific resistance value which is generally in the range of from about 0.01 to 10,000 ohm-cm—i.e. a specific conductance of 10,000 to 0.01 S/M. In a number of test cells produced in accordance with this invention, and depending on the measurement technique being used (either amperiometric or potentiometric or galvanostatic) the materials may have a specific resistance in the range of 0.1 to 1.000 ohm-cm. The material of the frame members 14 and 18 may also comprise conductive plastics that are used on electronic equipment for electromagnetic interference shielding. Such material is inexpensive, easily obtained, has acceptable specific resistance values, and is stable in the temperature ranges contemplated for the electrochemical sensor cells of the present invention. Typical materials include MAGNEX DC {TM} from Mitech Corporation, with a specific resistance of less than 1.0 ohm-cm.; SXO0.1{TM} from Polymer Concentrates, with a specific resistance of about 0. 1 ohm-cm.; RTP-HEC {TM} from RTP Co., with a specific resistance of about 0.1 ohm-cm. or less; and EBONEX, with a specific resistance of about 0.02 ohm-cm.

The material of the third frame member, the electrolyte frame member 20, may typically be polypropylene or ABS, which may be loaded with talcum. The material is chosen, in any event, so as to approximately match the thermal coefficient of expansion of the outer frame members. The third frame member may also comprise inert electronically and ionically non-conductive materials such as boron nitride, aluminum oxide, silica and various glasses, porcelain, etc., containing the ionic conductive electrolyte of choice.

As mentioned, the electrodes are porous, comprising at least one porous layer which may contain a catalytically active noble metal, or carbon, or they may comprise a porous or gas permeable conductive sintered matrix. Generally, the elecrtrodes will comprise a catalytically active noble metal dispersed in a high surface area form, carbon, EBONEX, or the like, with a polymeric hydrophobic binder such as PTFE. Such electrodes are described below.

The electrodes may also contain a metal mesh current collector, such as that indicated at 42 in FIG. 3.

By such structure, the electrochemical gas sensor cell of the present invention is essentially a fuel cell. So as to accommodate that type of arrangement, as shown in FIGS. 2, 3, 4, 5, and 7, the counter electrode is mounted in such a manner as to be exposed to an enclosed volume of scrubbed or otherwise uncontaminated air or gas. The gas could also be nitrogen. That is arranged by flooding the chamber 44 in the second frame member 18 with scrubbed air (or nitrogen), after which the chamber 44 is sealed with a plug or cap 46.

An alternative arrangement for the electrolyte 24 is shown in FIG. 3, where the electrolyte chamber 22 opens into a passage 48 which communicates with an electrolyte reservoir 50. As in the structure of FIG. 2, the electrolyte chamber is sealed with a plug 28.

Figure 4:
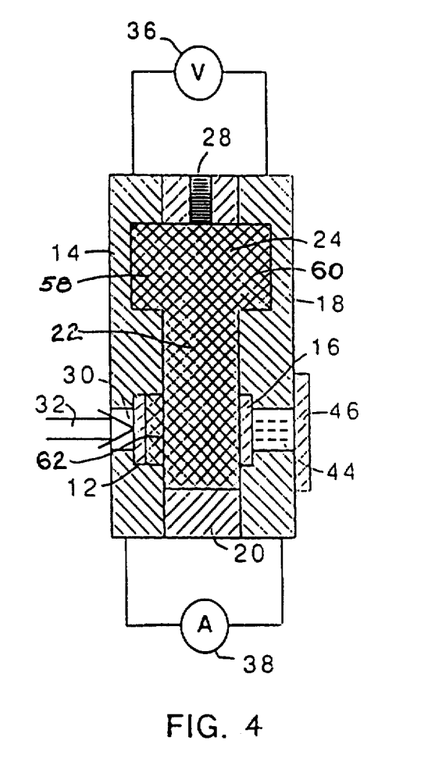

Another alternative arrangement for the electrolyte 24 is shown in FIG. 4 where the electrolyte chamber 22 extends into cavities 58 and 60 in frame members 14 and 18. There may also be a chamber 62 extending toward the sensor electrode 12. As in the structure of FIG. 2, the electrolyte chamber can be optionally sealed with a plug 28.

Figure 5:
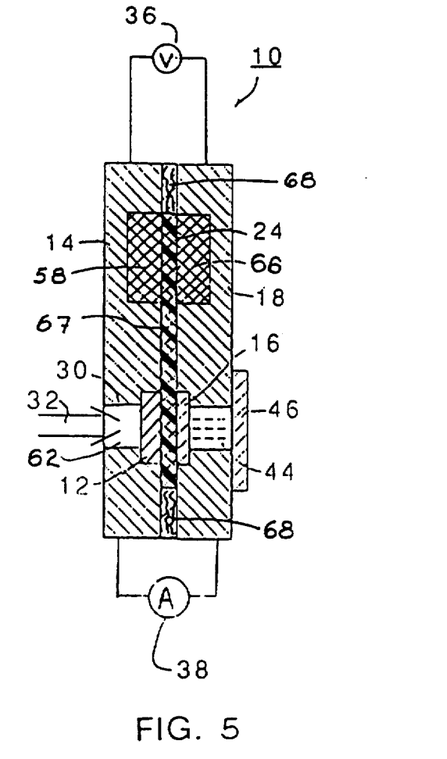

A further alternative arrangement for the electrolyte is shown in FIG. 5. Here, a substantial portion of the third frame member contains a solid electrolyte. A liquid reservoir such as water, in the case of a NAFION solid polymer electrolyte, can be incorporated into the first and second frame members, as at 58 and 66. The non-conductive frame member 67 may, in this case, only form an encirclement frame around the periphery of the solid electrolyte. Still further, the frame members may be attached to each other by using an adhesive or hot melt layer 68 applied between the surfaces to be joined.

Figure 6:
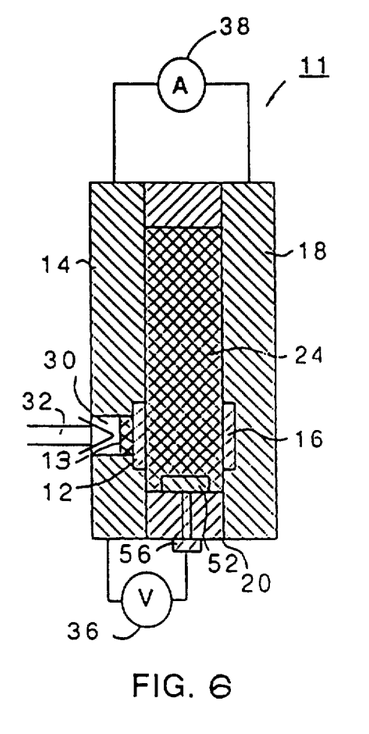

Referring briefly to the embodiment of FIG. 6, there is shown a sensor cell 11 having an additional electrode which is reference electrode 52, together with its electrical lead or contact pad 56. That reference electrode is located within the electrolyte chamber so as to be exposed to the electrolyte 24. Potentiometric measurement means, such as voltmeter 36, are provided in this embodiment between the sensor electrode 12 and the reference electrode 52; other electrical measurement means—for example, the ammeter 38—are provided between the sensor electrode 12 and the counter electrode 16. It is understood, of course, that either the frame members 14 and 18 are electrically conductive, or that additional conductors are included as necessary. In any event, an additional conductor such as shown at 56 would be provided between the reference electrode 52 and the exterior of the sensor cell 11 of FIG. 6.

Figure 7:
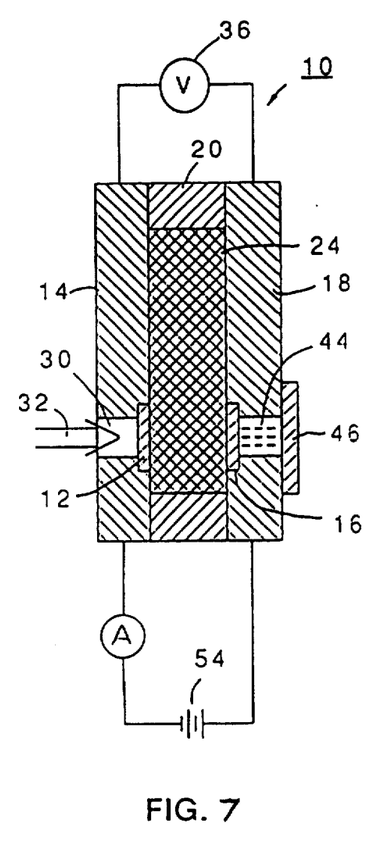

In yet another embodiment, as shown particularly in FIG. 7, the electrochemical gas sensor cell may be set up with an external power source 54. In that case, the external power source 54 provides a constant current flow through the sensor cell, and the voltage of the sensor electrode versus the counter or reference electrode is monitored. The ammeter 38, or alternatively the voltmeter 36, are shown as in a test set up, to ensure a steady constant current to the sensor cell, but are not needed in an actual installation.

In the embodiment of FIG. 7, a specific voltage is developed and maintained between the sensor electrode 12 and the counter electrode 16, which is measured by the voltmeter 36. However, in the presence of a contaminant gas being tested for, the potential between the sensor electrode 12 and the counter electrode 16 will change, and that change of electrical potential is detected and is indicative of the presence and also of the concentration of the contaminant gas being tested for.

Depending on the cell system, there may be in any of the embodiments of FIGS. 2 to 6, a specific electric potential developed between the sensor electrode 12 and the counter electrode 16 in the absence of the contaminant gas in the atmosphere being monitored. But, when there is a presence of the contaminant gas being tested for, there will be a predictable change of the voltage between the sensor electrode 12 and the counter electrode 16.

In other instances, there may be no or only an insignificant electrical potential developed between the sensor electrode 12 and the counter electrode 16, in the absence of a contaminant gas being tested for, and a readily detected electrical potential is developed in the presence of the contaminant.

In a two electrode structure such as that shown in FIGS. 2, 3, 4, or 5, the electrolyte may be a diluted sulphuric acid, in which case the material of the counter electrode 16 may comprise a porous storage electrode in order to obtain a stable reference voltage. That material may be lead, or oxides thereof. The cell operates, as do the others described herein, essentially as an air/metal battery with a very low capacity. But it is not the ampere-hour capacity of the cell that is a desired characteristic, it is the specific voltage between the sensor electrode and the counter electrode; so that a change of that voltage is indicative of the presence of a contaminant gas being tested for.

Generally, the rate of reaction of the electrochemical gas sensor cell is indicative of the concentration of the gas contaminant being tested for. In each instance, there is a particular anticipated voltage or trigger voltage level that should develop between the sensor electrode and the auxiliary electrode, which may be either the reference electrode or the counter electrode. In a typical circumstance, where carbon monoxide is being tested for, the presence of about 50 ppm (parts per million) could result in about 80% of the anticipated trigger voltage being reached in a period of about 5 minutes from the first exposure of the sensor electrode to that concentration. However, where the concentration is a more serious level such as 200 ppm or above, the response time of the cell would be within several seconds.

Several examples are given below of the manufacture of electrochemical gas sensor cells according to the present invention. In general, the gas sensor electrode 12 and the counter electrode 16 are mounted together, one on either side of and against the third frame member 20 or the encirclement frame 67. Suitable conductive materials must be chosen for the frame members 14 and 18 (or, when used, conductive wires or ribbons put in place) and a suitable non-conductive material must be chosen for the third frame member. Suitable materials have been discussed above. It is a characteristic of the present invention that the assembly of electrochemical gas sensor cells in keeping with this invention is accomplished quickly, and generally at temperatures that are less than about 300° C., or in any event less than 400° C.

Generally, the steps for assembly an electrochemical gas sensor cell according to the present invention are as follows:

a) choosing an inert conductive material and fabricating the first and second end frame members therefrom;
b) choosing an inert non-conductive material and fabricating the third frame member therefrom;
c) placing the material for the electrodes against the respective end frames to which the electrodes are to be bonded;
d) assembling the frame members and electrodes together; and
e) exposing the assembled frame members to appropriate conditions to form the sensor cell.

Depending on the material being used, for example polypropylene, step (e) may be carried out at about 165° C. for about 10 minutes, using a compression mould. Alternatively, it may be carried out in an induction furnace. When materials having a high melting point are used, the frame members may be joined using suitable adhesives or hot melts.

The present invention contemplates that, in some instances prior to step (d), at least one of each of the pairs of surfaces of the frame members that face each other—both surfaces of the third frame member or encirclement frame, and the inside surfaces of the first and second frame members that face them—is coated with a metallic oxide powder such as iron or titanium. Then, step (e) may be carried out in a microwave oven.

Alternatively, step (a) may be carried out after step (b) and as part of steps (c), (d), and (e), by placing the third frame member and the sensor electrode and counter electrode, one at each side thereof, in a mould. Then, the material of the first and second frame members may be injected into the mould in a fluid state, and thereafter permitted to harden.

In a specific example, conductive frame members were made from polypropylene filled with carbon, by placing the conductive granulate in a compression mould, and forming at 165° C. for 5 minutes. Porous electrodes having a PTFE structure with carbon are particularly useful in the present invention, because when they are heat bonded to the first and second frames, electrical contact between the electrode and the conductive frame is assured. At the same time, because of the hydrophobicity of the PTFE, electrolyte leakage is precluded. Moreover, by using temperatures below about 300° C., and in any event below 400° C., the sintering temperature of PTFE, the structural integrity of the electrodes is assured.

After placing an electrolyte matrix in the electrolyte chamber, the electrolyte plate was sandwiched between the two outer frame members together with the electrodes, and sandwiched in a compression mould at 165° C. for 10 minutes. Thereafter, the electrolyte filling port 26 was drilled, and electrolyte injected thereinto by vacuum filling.

In another example, carbon filled gas permeable paper or cloth may be dipped into PTFE, and thereafter gold deposited so as to have a high surface area onto that substrate. Then the components of the electrochemical cell are placed in an assembly jig and transferred into an induction furnace. In that instance, the conductive plastic plates heat up and melt into the two electrode structures, producing a conductive and liquid tight bond. At the same time, the softened conductive plastic frame members attach themselves to the nonconductive electrolyte plate—the third frame member——and a well secured electrochemical cell is assembled.

In other instances, as mentioned above, the surfaces of the components that are to face one another may be painted with a titanium oxide or iron oxide powder, for example, and then the assembly may be finished by curing in a microwave oven.

In other instances, as mentioned above, the surfaces of the components that are to face one another may be coated with adhesive. For example, the Down Corning silicon pressure sensitive X2-7656 using SYL OFF 7127 {TM} catalyst may be applied to the first and second frame members made of EBONEX, and the adhesive is cured between 15 to 15 minutes at 65° C. to 100° C. Thereafter, the components—including all three frame members—are aligned and pressed together whereby the pressure sensitive adhesive is activated and bonds the sensor cell firmly together.

As yet another alternative, pressure sensitive transfer tapes such as 5 mil SCOTCH Brand 9485 PC TM clear acrylic foam tape can be stamped out to the appropriate dimensions, and applied to the appropriate surfaces which need to be bonded.

In a still further alternative, the surfaces of the components to be joined can be coated with hot melt such as JET TM melt adhesive 3735 TM and after clamping, the hot melt is activated by raising the temperature to 170° C. for 5 minutes.

A solid polymer electrolyte sheet such as that sold in association the trade mark NAFION may have platinum electrodes sputtered, electrolessly plated, or electroplated onto it. Alteratively, gas diffusion electrodes such as SPE-CNM TM supplied by Elctrosynthesis Company Incorporated of Cheektowaga, N.Y., may be used. The gas diffusion electrodes may be optionally treated with liquid NAFION. Then, the sensor cell is formed by compression moulding at 165° C. for 10 minutes. Thereafter, the cell is activated by exposure to steam at 100° C.

Finally, an electrode paste containing platinum supported on carbon, EBONEX, or the like, together with a polymeric binder and a solvent may be screen printed onto a suitable electrolyte matrix, and then dried. Thereafter, the cell is formed in a compression mould and activated in the manner described above.

Cells manufactured according to the various processes noted above, and in keeping with the present invention, show remarkable consistence of performance, with rapid response in potentially dangerous concentrations of gases such as carbon monoxide. Long term operation has been demonstrated over periods of more than 12 months.

A typical cell according to the present invention may have dimensions as small as about 1.2 cm by 2.0 cm by 0.4 cm, or they may be larger or even smaller.

In keeping with the present invention, the porous sensing electrodes used in the electrochemical sensing cells discussed above comprise a layer which contains a catalytically active metal—usually a noble metal—or a metal oxide, together with carbon, EBONEX, or the like, and a polymeric binder, all in a suitable substrate.

The catalytic layer typically has a thickness of about 50 to 250 microns, containing the noble metal electrocatalyst. The noble metal particles in the layer are usually situated on the electrolyte side of the electrode; and the concentration of noble metal is typically less than 1.0 mg/cm$^2$.

To obtain maximum activity of the electrocatalyst being used, the material of choice is typically supported on a porous substrate such as carbon. Care is taken that the catalyst particles are sufficiently small to obtain a high surface area, since the electrocatalytic activity is linked to the surface area and not the catalyst weight. As an example, 10% platinum supported on VULCAN XC72R TM carbon, 20% Pt supported on BLACK PEARLS 2000 TM carbon, as may be supplied by the Electrosynthesis Company Incorporated of Cheektowaga, N.Y., may be utilized. In this case, the surface area of the noble metal ranges typically from 40 to 120 m$^2$/g —which is significantly higher than the noble metal blacks described by KITZELMANN and others. Typically, platinum black is a low surface area catalyst, having a surface area of less than 25 m$^2$/g.

As used herein, the term "noble metal" is taken in its wider sense, so that it is taken to include such metals as platinum, palladium, iridium, ruthenium, rhodium, gold, silver, and alloys and mixtures of two or more such metals.

In production, the catalytically active layer of the electrode may be made particularly thin by employing such methods as rolling, spraying, or screen printing. The active layer may be applied to a suitable substrate such as carbon cloth, felt or paper; or it may optionally be applied directly to a solid electrolyte matrix such as NAFION, cellulose, or DARAMIC.

The polymeric binder may be any suitable inert resin, particularly a hydrophobic compound. Examples of such binders include polyethyelne, polypropylene, polyvinlchloride, polystyrene, and PTFE. The loading of the binder may be in the range of 5% to 50% by weight of the porous electrode.

As noted, several different fabrication processes are suitable. For example, powdered carbon is mixed with a powder of a catalytically active noble metal on carbon and a binder. Catalytically active nobel metal particles may be contained by 10% ob 75% of the carbon particle. Moreover, the carbon may be mixed with or replaced by carbides, graphite, conductive oxides, borides, phosphides and the like. If desired or necessary, a pore former such as soluble salts may be incorporated in the mix, which is then typically pressed into an electrode and processed at an elevated temperature. In this manner, the pore former is removed.

It may be considered to apply a gas permeable membrane 13 at least on the gas side of the first sensor electrode 12, as shown in FIG. 6, for example, so as to reduce exchange of water. This is because the electrolyte may tend to dilute or become too concentrated, depending on its initial electrolyte concentration, as well as being affected by such factors as the temperature and humidity of the air in the environment being sensed.

The following examples set forth various typical compositions of electrodes that have been successfully tested in the gas sensors used to measure carbon monoxide, hydrogen, and other oxidizable gases.

Example 1:
Backing:
| | |
|---|---|
| Carbon Paper (Stackpole PC206 {TM}) | 50% |
| PTFE | 50% |

Active Layer:

-continued

| | | |
|---|---|---|
| VULCAN XC 72R {TM} | | 80% |
| PTFE | | 20% |
| Catalyst Loading: | 0.30 mg Platinum per cm² | |
| Example 2: | | |
| Backing: | | |
| Carbon Cloth (Stackpole PANEX {TM}) | | 50% |
| PTFE | | 50% |
| Diffusion Layer (Optional): | | |
| Acetylene Black | 25 g | 62.5% |
| PTFE | 15 g | 37.5% |
| Ammonium bicarbonate filler | 60 g | |
| Active Layer: | | |
| VULCAN XC 72R {TM} | | 89% |
| PTFE | | 11% |
| Catalyst Loading: | 0.3 mg Gold per cm² | |
| Example 3: | | |
| Backing: | | |
| Carbon Paper (Stackpole P105 {TM}) | | 50% |
| PTFE | | 50% |
| Active layer: | | |
| BLACK PEARLS {TM} | | 64% |
| PTFE | | 36% |
| Catalyst Loading: | 0.5 mg Palladium per cm² | |
| Example 4: | | |
| Backing: | | |
| Carbon Felt (Stackpole PANEX CFP 30-50 {TM}) | | 50% |
| PTFE | | 50% |
| Active Layer: | | |
| Acetylene Black | | 89% |
| PTFE | | 11% |
| Catalyst Loading: | 0.15 mg Platinum per cm² | |
| Example 5: | | |
| Backing: | | |
| Platinum Screen | | 50% |
| PTFE | | 50% |
| Diffusion Layer (Optional): | | |
| Acetylene Black | 25 g | 62.5% |
| PTFE | 15 g | 37.5% |
| Ammonium bicarbonate filler | 60 g | |
| Active Layer: | | |
| BLACK PEARLS {TM} | | 89% |
| Graphite | | 2% |
| PTFE | | 9% |
| Catalyst Loading: | 0.50 mg Palladium/ Rhodium per cm² | |

Figure 8:
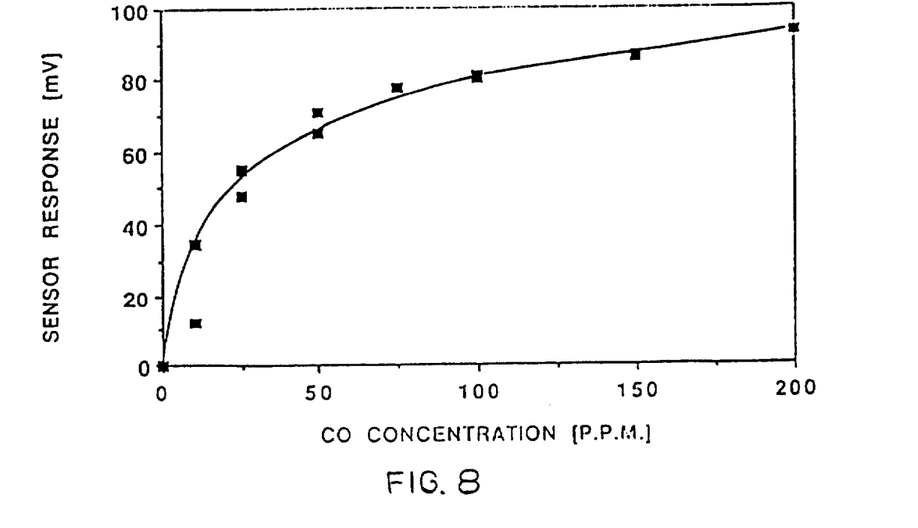
FIG. 8 shows a typical curve of potentiometric sensor output versus carbon monoxide gas concentration for a typical gas sensor cell according to this invention.
Figure 9:
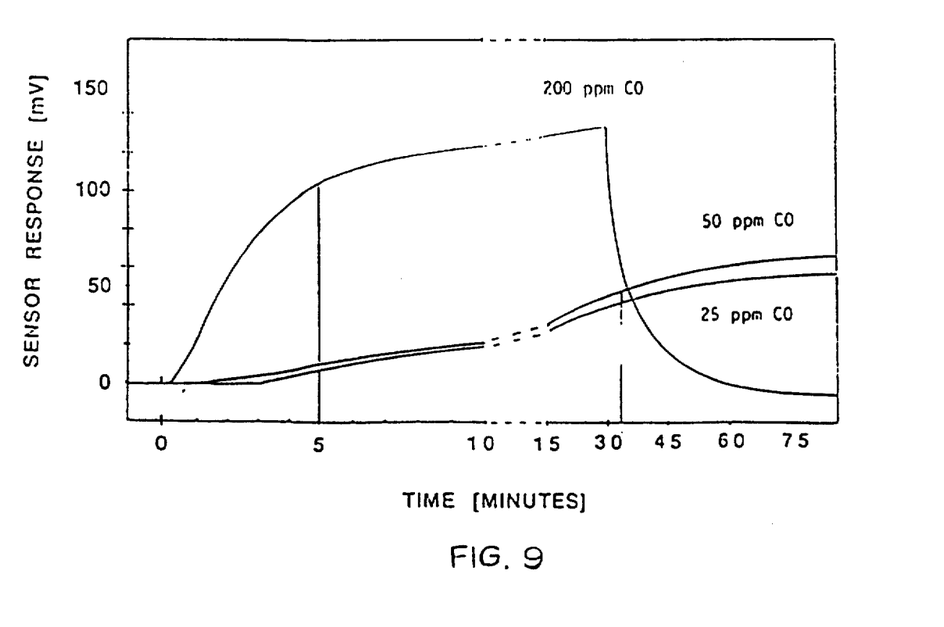
FIG. 9 shows typical response time characteristics of potentiometric sensor output for various gas contaminant concentrations.

A typical set of curves, showing the performance of a gas sensor having electrodes similar to those of Example 1 above is shown in FIGS. 8 and 9. In FIG. 8, the potentiometric response of the cell to various concentrations of CO in air is shown; and in FIG. 9 the time response to three different CO concentrations is shown. The electrolyte was phosphoric acid in each case.

It should be noted that, in each electrochemical gas sensor cell in keeping with the present invention, the catalyst material is wetted—or is at least capable of being partially wetted—by the electrolyte when it is exposed thereto. It is possible to pre-condition the cell by back-charging it —forcing current through the cell, in both directions—so as to enhance the wetting characteristics of the cell, especially one that has an aqueous electrolyte. It is also possible to add a hydrophilic substance such as surfactants or carboxy methyl cellulose (CMC) to the electrode mix; or even to add a hydrophilic binder such as polysulfone.

The examples noted above are exemplary, and the structure of the electrochemical gas sensor cells described above an shown in the drawings, are exemplary and not intended to be limited as to any specific cell.

The scope of the invention is defined in the appended claims.

What is claimed is:

1. An electrochemical gas sensor cell for quantitative measurement of gaseous or volatile contaminants in an atmosphere being monitored, said gas sensor cell comprising at least a first gas permeable porous sensor electrode mounted in a first frame member, a second counter electrode mounted in a second frame member, a third electrically non-conductive electrolyte encirclement member, an ion conductive electrolyte at least partially confined within an electrolyte chamber formed in said third electrolyte encirclement member, said first and second electrodes and said first and second frame members being located at first and second sides, respectively, of said electrolyte chamber such that at least a portion of each of said first sensor electrode and said second counter electrode contacts said electrolyte;

wherein at least one of said first and second frame members is electrically conductive, and conductor means is associated with the other of said first and second frame members when said other frame member is electrically non-conductive;

wherein said electrolyte is immobilized and confined in such a manner at to substantially accommodate changes in temperature or humidity of said atmosphere being monitored;

wherein said first sensor electrode and optionally also said second counter electrode contains a catalyst;

wherein electrolyte is incorporated into said porous sensor electrode, and wherein at least the catalyst contained in said porous sensor electrode is a high surface area catalyst having a surface area of at least 40 m²/g carried on a substrate and dispersed within said sensor electrode in such a manner that a three dimensional interface exists within the structure of said porous sensor electrode between said electrolyte, the electrocalytically active sites defined by said high surface area catalyst, and a gaseous or volatile contaminant that may be present in said atmosphere being monitored;

each of said first and second frame members and said electrolyte encirclement member being formed of an inert material which is impervious to said electrolyte;

said porous sensor electrode being mounted and secured with respect to said first frame member so as to be exposed to said atmosphere being monitored, and said counter electrode being mounted and secured with respect to said second frame member so as to be isolated from any exposure to said atmosphere being monitored; and wherein each of said first and second electrodes is connected to electrical measurement means;

whereby, when said atmosphere being monitored contains a gaseous or volatile contaminant for which the catalyst on said sensor electrode is chosen to produce a change in the electrical characteristic between said porous sensor electrode and said counter electrode when said porous sensor electrode is exposed to said gaseous or volatile contaminant in the presence of the chosen ion conductive electrolyte, said electrical measurement means detects the change of said electrical characteristics, which change is thereby indicative of the presence of said gaseous or volatile contaminants in said atmosphere being monitored.

2. The electrochemical gas sensor cell of claim 1, wherein said electrolyte is immobilized by being absorbed in a matrix contained within said electrolyte chamber.

3. The electrochemical gas sensor cell of claim 1, wherein said electrolyte is a wetted solid polymer or solid state electrolyte.

4. The electrochemical gas sensor cell of claim 3, wherein when said electrolyte is a solid polymer or an ion conductive solid state material, an amount of said electrolyte is incorporated into each of said first gas permeable porous sensor electrode and said second counter electrode.

5. The electrochemical gas sensor cell of claim 1, wherein said electrolyte chamber is in communication with an electrolyte reservoir above said electrolyte chamber.

6. The electrochemical gas sensor cell of claim 5, wherein said electrolyte chamber is formed in said electrolyte encirclement member and extends into at least one of said first and second frame members.

7. The electrochemical gas sensor cell of claim 1, wherein said first and second frame members are each formed of an electrically conductive plastics material, and thereby comprise said conductor means associated with said first and second electrodes.

8. The electrochemical gas sensor cell of claim 7, wherein the conductive plastics material of said first and second frame members is chosen from the group consisting of polypropylene, polyvinylidene difluoride, acrylonitrile butadiene styrene, polyvinyl chloride, and acrylonitrile butadiene; and wherein said conductive plastics material is filled with a conductive filler chosen from the group consisting of a metal, carbon, graphite, titanium oxide, tungsten carbide, and combinations thereof.

9. The electrochemical gas sensor cell of claim 1, wherein either of said first and second frame members is non-conductive.

10. The electrochemical gas sensor cell of claim 9, wherein the non-conductive material from which said non-conductive first or second frame member is made is chosen from the group consisting of polypropylene, polyvinylidene difluoride, acrylonitrile butadiene styrene, polyvinyl chloride, and acrylonitrile butadiene, or is a non-conductive ceramic chosen from the group consisting of boron nitride, aluminum oxide, silica, and glass.

11. The electrochemical gas sensor cell of claim 1, wherein at least one of said first and second frame members is an electrically conductive ceramic, metal oxide, metal carbide, or metal sulfide, chosen from the group consisting of $Ti_4O_7$, $Ti_xO_{2x-1}$ where $x = 5$ to 10, TiO, $Na_2WO_3$, WC, TiC, ZnC, $Cr_3C_2$, $WS_2$, $MoS_2$, borides and graphites, carbon and graphites, TiC+C, doped ceramics, and mixtures thereof.

12. The electrochemical gas sensor cell of claim 1, wherein said electrolyte encirclement member is substantially thinner than either of said first and second frame members.

13. The electrochemical gas sensor cell of claim 1, wherein said electrolyte is chosen from the group consisting of phosphoric acid, sulphuric acid, phosphoric acid diluted with distilled water, sulphuric acid diluted with distilled water, methanesulphonic acid, aqueous phosphate solutions, aqueous sulfate solutions, any of the above gelled with a gelling agent, and ionically conductive solid materials chosen from the group consisting of $Mag_4I_5$(M = Rb, K or Pb), $ZrO_2$, $H_2ZrP_2O_8 \cdot H_2O$, $HUP_2 \cdot PO_4 \cdot 4H_2O$, antimonic acid, $Ag_6I_4WO_4$, Na beta-alumina, $Na_3Zr_2Si_2PO_{12}$, and LiI.

14. The electrochemical gas sensor cell of claim 13, wherein, when said electrolyte is a solid electrolyte, a liquid reservoir is located in an adjacent electrolyte chamber which is connected to said solid electrolyte.

15. The electrochemical gas sensor cell of claim 13, wherein a membrane is applied to the gas side of said gas permeable porous sensor electrode when said electrolyte is aqueous, so as to suppress evaporation of water from said electrolyte.

16. The electrochemical gas sensor cell of claim 1, wherein said high surface area catalyst is chosen from the group consisting of platinum, palladium, iridium, gold, Pt/Pd alloy, Pd/Rh alloy, Au/Ru alloy, and organometallic compounds containing elements chosen from the group consisting of cobalt, iron, and nickel.

17. The electrochemical gas sensor cell of claim 16, wherein said catalyst is platinum, and said sensor cell is adapted to detect carbon monoxide in the range of up to 200 p.p.m.

18. The electrochemical gas sensor cell of claim 1, wherein said frame members and said electrolyte encirclement member are assembled together by placement of a suitable adhesive on opposing faces of said frame members and said electrolyte encirclement member; wherein the suitable adhesive is chosen from the group consisting of pressure sensitive adhesives, epoxies, hot melt adhesives, and pressure sensitive adhesive transfer tapes.

19. The electrochemical gas sensor cell of claim 1, wherein said electrolyte is a solid electrolyte which is capable of ionic motion within a solid lattice.

20. The electrochemical gas sensor cell of claim 1, wherein said gas sensor cell is adapted to test for a specific gas for which the catalyst on said sensor electrode is chosen, and where said second counter electrode is exposed to a contained volume of gas chosen from the group consisting of scrubbed air, cleaned air, nitrogen, air containing a known concentration of a gas chosen from the group consisting of carbon monoxide, hydrogen sulfide, hydrogen, and arsine, and combinations thereof, and gas containing a known concentration of a gas chosen from the group consisting of carbon monoxide, hydrogen sulfide, hydrogen, and arsine, and combinations thereof.

21. The electrochemical gas sensor cell of claim 20, where said counter electrode is non-polarizable.

22. The electrochemical gas sensor cell of claim 1, wherein said electrical measurement means is potentiometric, whereby a change in the voltage developed between said sensor electrode and said counter electrode may be detected and measured by said potentiometric measurement means.

23. The electrochemical gas sensor cell of claim 1, where said electrical measurement means is amperiometric.

24. The electrochemical gas sensor cell of claim 1, further comprising a reference electrode located so as to be exposed to said electrolyte; and wherein potentiometric measurement means are provided between said sensor electrode and said reference electrode, as well as said electrical measurement means between said sensor electrode and said counter electrode.

25. The electrochemical gas sensor cell of claim 1, wherein said sensor electrode is adapted to develop a specific electric potential in the absence of a contaminant gas in said atmosphere being monitored, and said specific electrical potential changes predictably in the presence of a contaminant gas.

26. The electrochemical gas sensor cell of claim 1, wherein said sensor electrode is adapted to develop a specific electric potential with respect to said counter electrode in the absence of a contaminant being tested for in said atmosphere being monitored, and wherein a readily detected and different electrode potential is developed in the presence of a contaminant gas.

27. The electrochemical gas sensor cell of claim 1, further comprising an external power source connected to said first sensing electrode and said second counter electrode so as to provide a constant current flow through said sensor cell;

whereby, a voltage is developed between said first and second electrodes which is measured by said electrical measurement means;

and whereby, when said atmosphere contains a gas contaminant for which the catalyst on said sensor electrode is chosen to produce a change in electrical potential with respect to said counter electrode when said sensor electrode is exposed to said gas contaminant in the presence of the chosen ion conductive electrolyte, said electrical measurement means detects the change of said electrical potential, which thereby is indicative of the presence of said gas contaminant.

28. The electrochemical gas sensor cell of claim 1, where said first porous sensor electrode and second electrode each comprises at least a porous catalytic layer containing particles of said high surface area catalyst; wherein said catalytic layer has a thickness of up to 250 microns, and the loading of said high surface area catalyst is in the range of between 0.1 and 1.0 mg/cm$^2$.

29. The electrochemical gas sensor cell of claim 28, where said catalytic layer has a thickness of from 25 to 250 microns.

* * * * *